US008183172B2

(12) United States Patent
Guillon et al.

(10) Patent No.: US 8,183,172 B2
(45) Date of Patent: *May 22, 2012

(54) DUAL ZEOLITE CATALYST COMPRISING A GROUP VIII METAL AND A GROUP IIIA METAL, AND ITS USE IN ISOMERIZATION OF AROMATIC C8 COMPOUNDS

(75) Inventors: Emmanuelle Guillon, Vernaison (FR); Eric Sanchez, Saint Genis Laval (FR); Sylvie Lacombe, Vernaison (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 641 days.

This patent is subject to a terminal disclaimer.

(21) Appl. No.: 12/158,534

(22) PCT Filed: Nov. 3, 2006

(86) PCT No.: PCT/FR2006/002361
§ 371 (c)(1),
(2), (4) Date: Oct. 29, 2008

(87) PCT Pub. No.: WO2007/080238
PCT Pub. Date: Jul. 19, 2007

(65) Prior Publication Data
US 2009/0299115 A1    Dec. 3, 2009

(30) Foreign Application Priority Data
Dec. 22, 2005  (FR) ..................... 05 13175

(51) Int. Cl.
*B01J 29/06*   (2006.01)
*C07C 5/22*    (2006.01)

(52) U.S. Cl. ............... 502/67; 502/60; 502/63; 502/64; 502/66; 502/71; 502/73; 502/74; 502/77; 502/78; 585/481

(58) Field of Classification Search ................... 502/60, 502/63, 64, 66, 67, 71, 73, 74, 77, 78; 585/481
See application file for complete search history.

(56) References Cited

U.S. PATENT DOCUMENTS

| | | | |
|---|---|---|---|
| 4,467,129 A | 8/1984 | Iwayama et al. | |
| 4,537,754 A | 8/1985 | Casci et al. | |
| 6,057,486 A | 5/2000 | Merlen et al. | |
| 6,576,581 B1 * | 6/2003 | Sharma et al. | 502/66 |
| 6,872,866 B1 | 3/2005 | Nemeth et al. | |
| 2001/0002426 A1 * | 5/2001 | Mohr et al. | 585/407 |
| 2005/0234279 A1 * | 10/2005 | Serra et al. | 585/475 |
| 2006/0100471 A1 * | 5/2006 | Serra Alfaro et al. | 585/475 |

FOREIGN PATENT DOCUMENTS
WO   WO 99/28031 A1   6/1999

* cited by examiner

*Primary Examiner* — Elizabeth Wood
(74) *Attorney, Agent, or Firm* — Millen, White, Zelano & Branigan, P.C.

(57) ABSTRACT

A catalyst is described which comprises at least one zeolite with structure type EUO, at least one zeolite selected from IM-5 zeolite and zeolites with structure type MFI, MOR, BEA and MTW, at least one group VIII metal, at least one group IIIA metal and at least one porous mineral matrix. The catalyst of the invention is used in a process for isomerizing a feed comprising aromatic compounds containing 8 carbon atoms per molecule.

17 Claims, No Drawings

DUAL ZEOLITE CATALYST COMPRISING A GROUP VIII METAL AND A GROUP IIIA METAL, AND ITS USE IN ISOMERIZATION OF AROMATIC C8 COMPOUNDS

TECHNICAL FIELD

The present invention relates to a catalyst formed from at least two distinct zeolites, one of which is a zeolite with structure type EUO, for use, for example, in aromatic hydrocarbon transformation reactions. More precisely, it concerns a catalyst for isomerizing aromatic compounds containing eight carbon atoms per molecule. The present invention also relates to the use of said catalyst in a process for isomerizing a feed comprising aromatic compounds containing eight carbon atoms per molecule.

PRIOR ART

In known processes for isomerizing aromatic compounds containing eight carbon atoms (AC8), a feed which is generally low in para-xylene with respect to the thermodynamic equilibrium of the mixture (i.e. with a much lower para-xylene content than that of a mixture at thermodynamic equilibrium at the temperature under consideration, that mixture comprising at least one compound selected from the group formed by meta-xylene, ortho-xylene, para-xylene and ethylbenzene) and generally rich in ethylbenzene compared with that same mixture at thermodynamic equilibrium, is introduced into a reactor containing at least one catalyst, under suitable temperature and pressure conditions to obtain at the reactor outlet a composition of aromatic compounds containing eight carbon atoms which is as close as possible to the composition of said mixture at thermodynamic equilibrium at the temperature of the reactor. From this mixture, para-xylene is then separated, optionally along with meta-xylene or ortho-xylene which are the desired isomers as they are of great importance, in particular for the synthetic fibre industry.

Catalysts used to carry out a process for isomerizing aromatic compounds containing eight carbon atoms are generally zeolitic catalysts. Prior art catalysts, in particular catalysts based on mordenite zeolite, only produce mediocre catalytic performances as non-negligible side reactions occurring in their presence generate losses. An example which may be cited of such secondary reactions is naphthene ring opening, which may or may not be followed by cracking (losses to paraffins) or disproportionation and transalkylation reactions of aromatics containing eight carbon atoms (losses to unwanted aromatic compounds), or hydrogenation of aromatic compounds (losses to naphthenes). Catalysts based on ZSM-5 zeolite, alone or mixed with other zeolites such as mordenite, for example, have already been used but also do not produce optimum catalytic performances. More recently, a catalyst has been proposed which is based on a zeolite with structure type EUO (EP-A1-0 923 987). The present invention thus proposes to provide a novel catalyst with a composition such that when it is used to isomerize aromatic compounds containing eight carbon atoms per molecule, secondary reactions are limited, thereby reducing losses.

SUMMARY OF THE INVENTION

The present invention provides a catalyst comprising at least one zeolite with structure type EUO, at least one zeolite selected from IM-5 zeolite and zeolites with structure type MFI, MOR, BEA and MTW, at least one metal from group VIII of the periodic table of the elements, at least one metal from group IIIA of the periodic table of the elements and at least one porous mineral matrix. Each of the zeolites included in the catalyst of the invention contains silicon and at least one element T selected from the group formed by aluminium, iron, gallium and boron, preferably aluminium.

The present invention also concerns the use of said catalyst in a process for isomerizing a feed comprising aromatic compounds containing eight carbon atoms per molecule.

ADVANTAGE OF THE INVENTION

It has surprisingly been discovered that a composite catalyst comprising a combination of at least one zeolite with structure type EUO, at least one zeolite selected from IM-5 zeolite and zeolites with structure type MFI, MOR, BEA and MTW, at least one group VIII metal and at least one group IIIA metal results in improved catalytic performances in reactions for isomerizing aromatic compounds containing eight carbon atoms per molecule. In particular, the catalyst of the invention limits secondary reactions substantially, thereby generating fewer losses, compared with prior art catalysts.

Further, by adjusting the relative quantity of the two zeolites, that with structure type EUO and that selected from IM-5 zeolite and zeolites with structure type MFI, MOR, BEA and MTW, in the catalyst of the invention, it is possible to process a very wide range of mixtures of hydrocarbon feeds.

DESCRIPTION

The present invention provides a catalyst comprising at least one zeolite with structure type EUO, at least one zeolite selected from IM-5 zeolite and zeolites with structure type MFI, MOR, BEA and MTW, at least one metal from group VIII of the periodic table of the elements, at least one metal from group IIIA of the periodic table of the elements and at least one porous mineral matrix.

In accordance with the invention, the catalyst comprises at least two zeolites with different structure types.

The zeolites present in the catalyst of the invention comprise silicon and at least one element T selected from the group formed by aluminium, iron, gallium and boron, preferably aluminium. They are preferably practically entirely in the acid form.

The zeolite with structure type EUO present in the catalyst of the invention has already been described in the art. It has a uni-dimensional microporous network with a pore diameter of 4.1×5.7 Å (1 Å=1 Angstrom=$10^{-10}$ m) ("Atlas of zeolite framework types", W M Meier, D H Olson and Ch Baerlocher, $5^{th}$ Edition, 2001). Further, N A Briscoe et al have disclosed, in an article in the review "Zeolites" (1988, 8, 74) that uni-dimensional channels have side pockets with a depth of 8.1 Å and a diameter of 6.8×5.8 Å. The zeolite with structure type EUO includes the zeolites EU-1 (EP-B1-0 042 226), ZSM-50 (U.S. Pat. No. 4,640,829) and TPZ-3 (EP-A1-0 051 318). The zeolite with structure type EUO present in the catalyst of the invention is preferably an EU-1 zeolite. Said zeolite with structure type EUO is characterized by a Si/T atomic ratio, preferably an Si/Al atomic ratio, of at least 5, advantageously in the range 5 to 100. Said zeolite with structure type EUO is at least partially, preferably practically completely in the acid form, i.e. in the hydrogen form $H^+$, the sodium content preferably being such that the atomic ratio Na/T is less than 0.1, preferably less than 0.05 and more preferably less than 0.01. A mode for synthesizing an EU-1 zeolite is described in EP-B1-0 042 226. A mode for synthesizing a ZSM-50 zeolite is described in U.S. Pat. No. 4,640, 829. A mode for synthesizing a TPZ-3 zeolite is described in EP-A1 0 051 318.

The catalyst of the invention also comprises at least one zeolite selected from IM-5 zeolite and zeolites with structure type MFI, MOR, BEA and MTW. Preferably, said zeolite selected from IM-5 zeolite and zeolites with structure type MFI, MOR, BEA and MTW is characterized by an Si/T atomic ratio, preferably a Si/Al atomic ratio, in the range 2 to 250, preferably in the range 5 to 150 and more preferably in the range 10 to 80. The sodium content is less than 0.2% by weight, preferably less than 0.1% by weight and more preferably less than 0.05% by weight with respect to the total dry zeolite weight. Zeolites with structure type MFI, MOR, BEA and MTW have been catalogued in the zeolites atlas ("Atlas of zeolite framework types", W M Meier, D H Olson and Ch Baerlocher, $5^{th}$ Edition, 2001) and are synthesized using the methods described in the references cited in that work or using any other method described in the literature which is available to the skilled person. Any commercially available zeolite may also be used to prepare the catalyst of the invention. Highly advantageously, the zeolite selected from IM-5 zeolite and zeolites with structure type MFI, MOR, BEA and MTW is selected from IM-5, ZSM-5, mordenite, beta and ZSM-12 zeolites. IM-5 zeolite has been described in patents EP-B-0 946 416 and U.S. Pat. No. 6,136,290.

The crystals of the zeolite with structure type EUO and those of the zeolite selected from IM-5 zeolite and zeolites with structure type MFI, MOR, BEA and MTW are clearly distinguished from each other; there is no overlap.

The atomic ratio Si/T, preferably the atomic ratio Si/Al of the zeolite with structure type EUO and that of the zeolite selected from IM-5 zeolite and zeolites with structure type MFI, MOR, BEA and MTW are those obtained after synthesis of said zeolites, or those obtained after post-synthesis extraction of a portion of the T atoms, termed dealumination treatments when the element T is aluminium, which are well known to the skilled person; non-exhaustive examples are hydrothermal treatments which may or may not be followed by acid attacks or direct acid attacks using solutions of mineral or organic acids to extract a portion of the T atoms, preferably a portion of the aluminium atoms from the zeolitic framework.

The atomic ratio Si/T, preferably the atomic ratio Si/Al, of the zeolite with structure type EUO and of the zeolite selected from IM-5 zeolite and zeolites with structure type MFI, MOR, BEA and MTW forming part of the composition of the catalyst of the invention and the chemical composition of said catalyst are determined by X ray fluorescence and atomic absorption.

The zeolites forming part of the composition of the catalyst of the invention may be calcined and exchanged by at least one treatment using a solution of at least one ammonium salt to obtain the ammonium form of the zeolites which, once calcined, produce the hydrogen form of said zeolites.

The zeolites forming part of the composition of the catalyst of the invention are at least partially, preferably practically entirely in the acid form, i.e. in the hydrogen form ($H^+$). The atomic ratio Na/T is generally less than 10%, preferably less than 5% and still more preferably less than 1%.

The catalyst of the invention also comprises at least one metal from group VIII of the periodic table of the elements and at least one metal from group IIIA of the periodic table of the elements. The weight content of each metal is preferably in the range 0.01% to 5%, preferably in the range 0.05% to 3% and more preferably in the range 0.2% to 2% by weight with respect to the total weight of said catalyst. Preferably, the group VIII metal is a noble metal, preferably platinum. Preferably, the group IIIA metal is indium. The catalyst of the invention may optionally also comprise at least one group IVA metal, preferably in a quantity in the range 0.01% to 5% and more preferably in the range 0.5% to 3% by weight with respect to the total catalyst weight. Highly advantageously, said group IVA metal is tin. Said group IVA metal can advantageously increase the stability of the catalyst of the invention.

The porous mineral matrix, preferably present in an amount in the range 10% to 98%, preferably in the range 20% to 95%, more preferably in the range 60% to 95% by weight with respect to the total catalyst weight, is generally selected from elements from the group formed by clays (for example natural clays such as kaolin, sepiolite, attapulgite or bentonite), magnesia, aluminas, silicas, titanium oxide, boron oxide, zirconia, aluminium phosphates, titanium phosphates, zirconium phosphates, amorphous silica-aluminas and coal, preferably from elements of the group formed by aluminas, clays, mixtures of alumina and silica and mixtures of alumina and silica-alumina, and more preferably from aluminas and in particular gamma alumina.

In general, and in a first implementation of the preparation of the catalyst of the invention, the catalyst is prepared by mixing at least one zeolite with structure type EUO and at least one zeolite selected from IM-5 zeolite and zeolites with structure type MFI, MOR, BEA and MTW, said zeolites being in the powder state. The mixture of said zeolites is produced using any powder mixing technique known to the skilled person. Once the mixture of zeolite powders has been produced, the mixture is formed using any technique which is known to the skilled person. In particular, it may be mixed with a porous mineral matrix, generally amorphous, for example with a moist alumina gel powder. The mixture is then formed, for example by extrusion through a die. Forming may be carried out with matrices other than alumina, such as magnesia, amorphous silica-aluminas, natural clays (kaolin, bentonite, sepiolite, attapulgite), silica, titanium oxide, boron oxide, zirconia, aluminium phosphates, titanium phosphates, zirconium phosphates, coal and mixtures thereof. Preferably, matrices containing alumina are used, in any of the forms known to the skilled person, and more preferably gamma alumina. It may also be advantageous to use mixtures of alumina and silica, or mixtures of alumina and silica-alumina. Techniques other than extrusion, such as pelletization or bowl granulation, may be used. After the forming step, the catalytic support obtained undergoes a drying step carried out at a temperature in the range 80° C. to 150° C. then a calcining step carried out at a temperature in the range 300° C. to 600° C., preferably in the range 400° C. to 550° C.

The metals from groups IIIA and VIII and optional metal from group IVA are deposited onto at least one catalytic support after forming zeolites which are free of metals, using any process which is known to the skilled person and which can allow a metal to be deposited onto the catalytic support. The term "catalytic support" means a mixture of at least one zeolite with structure type EUO, at least one zeolite selected from IM-5 zeolite and zeolites with structure type MFI, MOR, BEA and MTW (metal-free zeolites) with at least one porous mineral matrix after forming, drying and calcining as described above. Said catalytic support of the catalyst of the present invention generally has the following quantities of matrix and zeolites:

2% to 90% by weight, preferably 5% to 80% by weight, more preferably 5% to 40% by weight of zeolites such that at least one zeolite is a zeolite with structure type EUO and at least one zeolite is a zeolite selected from IM-5 zeolite and zeolites with structure type MFI, MOR, BEA and MTW;

10% to 98% by weight, preferably 20% to 95% by weight, more preferably 60% to 95% by weight of at least one amorphous or low crystallinity oxide type porous mineral matrix.

In accordance with a second implementation for the preparation of the catalyst of the invention, prior to forming, at least one of the zeolites described above, i.e. at least one zeolite with structure type EUO or at least one zeolite selected from IM-5 zeolite and zeolites with structure type MFI, MOR, BEA and MTW, comprised in said catalyst undergoes deposition of at least one metal selected from metals from groups IIIA and VIII, optionally group IVA. In particular, the deposition of at least one metal from group VIII and at least one group IIIA metal onto the same zeolite or the deposition of at least one group VIII metal on one zeolite and at least one group IIIA metal on the other zeolite may be envisaged. The zeolites, at least one of which is charged with metal(s), are then mixed. Mixing of said zeolites, at least one of which is charged with metal(s), which are still in the powder state, is carried out using any powder mixing technique known to the skilled person.

Once the mixture of zeolite powders has been formed, wherein at least one of the powders is charged with metal(s), the mixture is formed using any technique which is known to the skilled person. In particular, it may be mixed with a porous mineral matrix, generally amorphous, for example a moist alumina gel powder. The mixture is then formed, for example by extrusion through a die. Forming may be carried out with matrices other than alumina, such as magnesia, amorphous silica-aluminas, natural clays (kaolin, bentonite, sepiolite, attapulgite), silica, titanium oxide, boron oxide, zirconia, aluminium phosphates, titanium phosphates, zirconium phosphates, coal and mixtures thereof. Preferably, matrices containing alumina are used, in any of the forms known to the skilled person, and more preferably gamma alumina. It may also be advantageous to use mixtures of alumina and silica, or mixtures of alumina and silica-alumina. Techniques other than extrusion, such as pelletization or bowl granulation, may be used. After the forming step, the catalytic support obtained undergoes a drying step carried out at a temperature in the range 80° C. to 150° C. then a calcining step carried out at a temperature in the range 300° C. to 600° C., preferably in the range 400° C. to 550° C.

To deposit the metals from groups IIIA and VIII and optional metal from group IVA on at least one zeolite with structure type EUO and/or onto at least one zeolite selected from IM-5 zeolite and zeolites with structure type MFI, MOR, BEA and MTW and/or onto the catalytic support in accordance with the first or the second mode for preparing the catalyst of the invention, it is possible to use a technique for cationic exchange with competition, wherein the competitor is preferably ammonium nitrate, the competition ratio between the competitor and the metallic precursor being at least about 5 and advantageously in the range 5 to 200. The dry impregnation or co-precipitation technique may also be used.

The sources of group VIII metals which may be used are well known to the skilled person. Examples which may be used are nitrates, sulphates, phosphates, halides, for example chlorides, bromides or fluorides, carboxylates, for example acetates and carbonates. In the case of platinum, hexachloroplatinic acid is preferably used. Sources of group IIIA metals which may be used are also well known to the skilled person. For indium, indium nitrate or indium chloride is preferably used. Sources of group IVA metals which may be used are also well known to the skilled person. For tin, tin chloride or tetrabutyl tin is preferably used. Deposition of the group VIII and group IIIA and optional group IVA metals is generally followed by calcining in air or oxygen, usually between 300° C. and 600° C. for 0.5 to 10 hours, preferably between 350° C. and 550° C. for 1 to 4 hours. Next, reduction in hydrogen may be carried out, generally at a temperature in the range 300° C. to 600° C. for 1 to 10 hours, preferably between 350° C. and 550° C. for 2 to 5 hours.

In said first or said second implementation for preparing the catalyst of the invention, the metals may also be deposited not directly on the zeolites but on the porous mineral matrix (for example the alumina binder) of the catalytic support, before or after the forming step, using anionic exchange. In general, after depositing the metal, as before, the catalyst undergoes calcining then reduction in hydrogen as indicated above.

The metals from groups VIII and IIIA, and optionally from group IVA, are introduced either in the same manner or using different techniques, before or after forming depending on the catalyst preparation mode employed, and in any order. In the case in which the technique used is ion exchange, several exchanges in succession may be necessary to introduce the required quantities of metals.

Regardless of the mode for preparing the catalyst of the invention, after calcining said catalyst, reduction may be carried out in hydrogen, generally at a temperature in the range 300° C. to 600° C., preferably in the range 350° C. to 550° C., for a period in the range 1 to 10 hours, preferably 2 to 5 hours. Such a reduction may be carried out ex situ or in situ, with respect to the place of use of said catalyst in a given reaction.

The distribution between the two zeolites present in the catalyst of the invention is such that the quantity of zeolite with structure type EUO may be from 1% to 99%, preferably 5% to 95% and more preferably 10% to 90%, as a percentage by weight of the zeolite with structure type EUO with respect to the total zeolites introduced into the catalyst. Similarly, the quantity of zeolite selected from IM-5 zeolite and zeolites with structure type MFI, MOR, BEA and MTW is from 1% to 99%, preferably 5% to 95% and more preferably 10% to 90%, as a percentage by weight of said zeolite with respect to the total quantity of zeolites introduced into the catalyst.

The catalyst of the present invention is formed into grains with different shapes and dimensions. It is generally used in the form of cylindrical extrudates or polylobed extrudates such as bilobes, trilobes, or polylobes with a straight or twisted shape, but may optionally be manufactured and used in the form of powder, pellets, tablets, rings, beads or wheels.

The catalyst of the present invention may optionally contain sulphur. In this case, the sulphur is introduced into the formed and calcined catalyst containing the element(s) cited above, either in situ before the catalytic reaction or ex situ. Sulphurization is carried out using any sulphurizing agent which is known to the skilled person, such as dimethyldisulphide or hydrogen sulphide. Any sulphurization is carried out after reduction. In the case of in situ sulphurization, reduction, if the catalyst has not already been reduced, is carried out before sulphurization. In the case of ex situ sulphurization, reduction is carried out followed by sulphurization.

The invention also concerns the use of the catalyst of the invention in processes for converting hydrocarbons. More precisely, the present invention concerns a process for isomerizing a feed comprising aromatic compounds containing eight carbon atoms per molecule carried out in the presence of a catalyst in accordance with the invention. Said feed comprises a mixture of xylenes and ethylbenzene. Said process is preferably carried out in the gas phase, in the absence of any liquid phase. Said process is generally carried out under the following operating conditions:

- a temperature in the range 300° C. to 500° C., preferably in the range 320° C. to 450° C. and more preferably in the range 340° C. to 430° C.;
- a partial pressure of hydrogen in the range 0.3 to 1.5 MPa, preferably in the range 0.4 to 1.2 MPa and more preferably in the range 0.7 to 1.2 MPa;
- a total pressure in the range 0.45 to 1.9 MPa, preferably in the range 0.6 to 1.5 MPa;
- an hourly space velocity, expressed in kilograms of feed introduced per kilogram of catalyst per hour, in the range 0.25 to 30 $h^{-1}$, preferably in the range 1 to $10^{-1}$, and more preferably in the range 2 to 6 $h^{-1}$.

The following examples illustrate the invention without in any way limiting its scope.

EXAMPLE 1

Preparation of a Catalyst Based on a ZSM-5 Zeolite and a Mordenite Zeolite and Comprising Platinum (Comparative)

The mordenite zeolite used to prepare the catalyst of this example 1 was a commercial zeolite sold by Zeolyst. It had a Si/Al ratio, measured by X-ray fluorescence, of 10.0 and a residual sodium content of 109 ppm. It was in its acid form.

The ZSM-5 zeolite used to prepare the catalyst of this example 1 was a commercial zeolite sold by Zeolyst. It had a Si/Al ratio, measured using X-ray fluorescence, of 17.5 and a residual sodium content of 132 ppm. It was in its acid form.

The ZSM-5 zeolite and the mordenite zeolite which were in the powder state were then mechanically mixed and formed by extrusion with an alumina gel to obtain, after drying overnight at 100° C. and calcining at 500° C. in dry air, a support which contained 15% by weight of zeolites (ZSM-5+mordenite) and 85% of alumina. The ZSM-5 and mordenite zeolites were present in an equivalent amount by weight in the support (50/50 weight distribution). The zeolitic support underwent dry impregnation using a solution of hexachloroplatinic acid $H_2PtCl_6$ so as to introduce 0.3% by weight of platinum with respect to the weight of catalyst. The moist solid was then dried at 120° C. for 12 hours and calcined in a stream of dry air at a temperature of 500° C. for one hour. Catalyst A obtained contained 7.5% by weight of EU-1 zeolite in the H form, 7.5% of ZSM-5 zeolite in the H form, 84.7% of alumina and 0.3% of platinum.

EXAMPLE 2

Preparation of Bi-zeolitic Catalysts Wherein one Zeolite is an EU-1 Zeolite, and Comprising Platinum and Indium (in Accordance with the Invention)

The zeolites used to prepare the catalysts illustrating the invention are shown in Table 1 with their composition (Si/Al atomic ratio) and their residual sodium content. The zeolites concerned were all in the acid form.

For the EU-1 zeolite, the starting material used was an as synthesized EU-1 zeolite comprising the organic template, silicon and aluminium, with an overall Si/Al atomic ratio of 13.6, a sodium content, by weight with respect to the weight of dry EU-1 zeolite, of about 1.5%, corresponding to an atomic ratio Na/Al of 0.6. This EU-1 zeolite initially underwent "dry" calcining at 550° C. in a stream of air for 6 hours. Next, the solid obtained underwent three ion exchanges in a 10N $NH_4NO_3$ solution at about 100° C. for 4 hours for each exchange. At the end of these treatments, the EU-1 zeolite in the $NH_4$ form had an Si/Al atomic ratio of 18.3, and a sodium content, by weight with respect to the weight of dry EU-1 zeolite, of 50 ppm, corresponding to a Na/Al atomic ratio of 0.003.

The beta, mordenite and ZSM-5 zeolites are commercially available zeolites (Zeolyst). The IM-5 zeolite was synthesized in accordance with Example n° 1 of European patent application EP-A-0 946 416 or U.S. Pat. No. 6,136,290 the contents of which are hereby incorporated by reference.

TABLE 1

Characteristics of zeolites used in the invention

| Zeolites | Si/Al (XRF) | Na (ppm) |
| --- | --- | --- |
| Beta | 12.5 | 87 |
| ZSM-5 | 17.5 | 132 |
| Mordenite | 10.0 | 109 |
| IM-5 | 12.0 | 84 |
| EU-1 | 18.3 | 50 |

All of the zeolites were in the powdered state. The EU-1 zeolite, which was in the powdered state, was then mechanically mixed with another type of zeolite (beta, ZSM-5, mordenite or IM-5) then the ensemble was formed by extrusion with an alumina gel to obtain, after drying at 100° C. overnight and calcining at 500° C. in dry air, a support which contained, by weight, 15% of zeolites (an EU-1 zeolite in combination with another type of zeolite) and 85% alumina. The weight distribution of the zeolites in the zeolitic support and the type of zeolites present in each support are given in Table 2.

To prepare catalysts B, C, D and E, the zeolitic support comprising a mixture of 2 different zeolites (EU-1+mordenite for catalyst B, EU-1+beta for catalyst C, EU-1+ZSM-5 for catalyst D and EU-1+IM-5 for catalyst E) initially underwent dry impregnation with a solution of hexachloroplatinic acid $H_2PtCl_6$ to introduce 0.3% by weight of platinum with respect to the catalyst weight. The solid which had been impregnated was dried overnight at 120° C. then underwent dry impregnation with an indium nitride solution to deposit 0.3% by weight of indium with respect to the weight of catalyst. The moist solid was then dried at 120° C. for 12 hours and calcined in a stream of dry air at a temperature of 500° C. for one hour. The compositions of the catalysts obtained are shown in Table 2.

Catalyst F was prepared in the same manner as catalyst B, impregnation with indium nitride immediately being followed by dry impregnation with a solution of tin chloride to introduce 0.3% by weight of tin with respect to the weight of catalyst F.

TABLE 2

| Catalyst | Zeolite(s) | Distribution of zeolites | % by weight of metal |
| --- | --- | --- | --- |
| B | EU-1 + mordenite | 50/50 | 0.3% Pt, 0.3% In |
| C | EU-1 + beta | 75/25 | 0.3% Pt, 0.3% In |
| D | EU-1 + ZSM-5 | 75/25 | 0.3% Pt, 0.3% In |
| E | EU-1 + IM-5 | 75/25 | 0.3% Pt, 0.3% In |
| F | EU-1 + mordenite | 50/50 | 0.3% Pt, 0.3% In, 0.3% Sn |

EXAMPLE 3

Evaluation of Catalytic Properties of Catalysts A to F by Isomerization of an Aromatic C8 Cut The performances of catalysts A to F were evaluated by isomerizing an aromatic cut comprising aromatic compounds containing eight carbon atoms per molecule, principally meta-xylene, ortho-xylene and ethylbenzene. The operating conditions employed were as follows:

temperature=390° C.;
pressure=15 bars;
partial pressure of $H_2$=12 bars.

The catalysts were pre-treated with a feed containing dimethyldisulphide (DMDS) in the presence of hydrogen, with a concentration such that the atomic ratio of sulphur to metal was 1.5. The catalysts were then kept for 3 hours at 400° C. in a stream of hydrogen and the feed was then injected.

The hourly space velocities were adjusted for each catalyst to ensure isoconversion of ethylbenzene. The catalysts were compared in terms of selectivity by their net losses at ethylbenzene isoconversion.

The isomerization reaction leads to side reactions generating three types of losses: losses to paraffins, essentially resulting from naphthene ring opening reactions followed by cracking, losses to aromatics formed by disproportionation and transalkylation of aromatics containing 8 carbon atoms (AC8), and finally losses to napthenes including napthenes containing 8 carbon atoms (N8) due to aromatic hydrogenation. Since the N8s can be recycled, the losses by cracking and disproportionation/transalkylation including naphthenes other than N8 (the sum of which constitutes the net losses) will be compared.

The losses by cracking (P1) are losses of AC8 in the form of C1 to C8 paraffins (PAR):

$$P1\ (wt\ \%)=100\times[(\%\ PAR_{effluent}\times\text{effluent weight})-(\%\ PAR_{feed}\times\text{weight of feed})]/(\%\ AC8_{feed}\times\text{wt of feed}).$$

The losses by disproportionation/transalkylation (P2) are losses of AC8 in the form of naphthenes other than N8, of toluene, of benzene and of C9+aromatics (OAN):

$$P2\ (wt\ \%)=100\times[(\%\ OAN_{effluent}\times\text{effluent weight})-(\%\ OAN_{feed}\times\text{weight of feed})]/(\%\ AC8_{feed}\times\text{wt of feed}).$$

The sum of losses P1 and P2 represents the net losses.

The data shown in Table 3 were obtained at isoconversion of ethylbenzene (61%).

TABLE 3

Catalytic evaluation of catalysts A to F.

| | Catalyst | | | | | |
|---|---|---|---|---|---|---|
| | A | B | C | D | E | F |
| Net losses (wt %) | 4.9 | 4.1 | 4.2 | 4.4 | 4.5 | 4.1 |

Catalysts B to F in accordance with the invention which each comprise a zeolite with structure type EUO and a zeolite selected from mordenite zeolites (catalysts B and F), beta zeolites (catalyst C), ZSM-5 zeolite (catalyst D) and IM-5 zeolite (catalyst E) as well as platinum and indium, exhibited reduced net losses, meaning that secondary reactions were limited compared with the performances obtained using catalyst A which was free of indium.

The invention claimed is:

1. A catalyst comprising at least one zeolite with structure type EUO, at least one zeolite selected from IM-5 zeolite and zeolites with structure type MFI, MOR, BEA and MTW, platinum, indium and at least one porous mineral matrix.

2. A catalyst according to claim 1, in which the zeolite with structure type EUO is an EU-1 zeolite.

3. A catalyst according to claim 1, in which the zeolite selected from IM-5 zeolite and zeolites with structure type MFI, MOR, BEA and MTW is selected from IM-5, ZSM-5, mordenite, beta and ZSM-12 zeolites.

4. A catalyst according to claim 1, further comprising at least one group IVA metal.

5. A catalyst according to claim 4, in which said group IVA metal is tin.

6. A catalyst according to claim 1, comprising sulphur.

7. A catalyst according to claim 2, in which the zeolite selected from IM-5 zeolite and zeolites with structure type MFI, MOR, BEA and MTW is selected from IM-5, ZSM-5, mordenite, beta and ZSM-12 zeolites.

8. A catalyst according to claim 2, further comprising at least one group IVA metal.

9. A catalyst according to claim 8, in which said group IVA metal is tin.

10. A catalyst according to claim 8, comprising sulphur.

11. A catalyst according to claim 9, comprising sulphur.

12. A catalyst according to claim 2, wherein the EU-1 zeolite is present in a concentration of 10% to 90% by weight of the zeolites in the catalyst.

13. A catalyst according to claim 12, comprising an EU-1 zeolite and a mordenite zeolite.

14. A catalyst according to claim 13, further comprising tin and sulphur.

15. A process for isomerizing a feed comprising aromatic compounds containing eight carbon atoms per molecule, carried out in the presence of a catalyst in accordance with claim 1.

16. An isomerization process according to claim 15, in which said feed comprises a mixture of xylenes and ethylbenzene.

17. An isomerization process according to claim 15, carried out at a temperature in the range 300° C. to 500° C. with a partial pressure of hydrogen in the range 0.3 to 1.5 MPa, with a total pressure in the range 0.45 to 1.9 MPa and at an hourly space velocity, expressed in kilograms of feed introduced per kilogram of catalyst per hour, in the range 0.25 to 30 $h^{-1}$.

* * * * *